United States Patent

Proto et al.

[11] Patent Number: 5,569,302
[45] Date of Patent: Oct. 29, 1996

[54] TIPPED MULTIFILAMENT SURGICAL SUTURE

[75] Inventors: George R. Proto, West Haven; Francis D. Colligan, Waterbury; Harold Bellmore, Jr., West Haven, all of Conn.

[73] Assignee: United States Surgical Corporation, Norwalk, Conn.

[21] Appl. No.: 400,710

[22] Filed: Mar. 3, 1995

Related U.S. Application Data

[62] Division of Ser. No. 122,072, Sep. 14, 1993, Pat. No. 5,425,746, which is a division of Ser. No. 7,361, Jan. 21, 1993, Pat. No. 5,269,808, which is a continuation of Ser. No. 626,995, Dec. 13, 1990, abandoned.

[51] Int. Cl.⁶ .................................................. A61B 17/04
[52] U.S. Cl. ........................... 606/228; 606/230; 606/231
[58] Field of Search ................................... 606/224–231, 606/228–231

[56] References Cited

U.S. PATENT DOCUMENTS

| | | |
|---|---|---|
| 2,734,506 | 2/1956 | Nichols et al. . |
| 2,794,788 | 6/1957 | Coover, Jr. et al. . |
| 2,928,395 | 3/1960 | Forbes et al. . |
| 3,212,502 | 10/1965 | Myers . |
| 3,394,704 | 7/1968 | Dery . |
| 3,527,650 | 9/1970 | Block . |
| 3,540,452 | 11/1970 | Usher et al. . |
| 3,667,472 | 6/1972 | Halpern . |
| 3,700,489 | 10/1972 | Borysko . |
| 3,736,646 | 6/1973 | Schmitt et al. . |
| 3,849,185 | 11/1974 | Sheperd . |
| 3,890,975 | 6/1975 | McGregor . |
| 3,896,077 | 7/1975 | Leonard et al. . |
| 3,963,031 | 6/1976 | Hunter . |
| 3,980,177 | 9/1976 | McGregor . |
| 3,999,970 | 12/1976 | Barch et al. . |
| 4,027,676 | 6/1977 | Mattei . |
| 4,042,442 | 8/1977 | Dombroski et al. . |
| 4,057,535 | 11/1977 | Lipatova et al. . |
| 4,127,133 | 11/1978 | Martinez . |
| 4,185,637 | 1/1980 | Mattei . |
| 4,344,382 | 2/1982 | Hausler et al. . |
| 4,412,505 | 11/1983 | Hausler et al. . |
| 4,506,672 | 3/1985 | Bichon . |
| 4,511,686 | 4/1985 | Millet . |
| 4,526,808 | 7/1985 | Strohmaier . |
| 4,595,600 | 6/1986 | Keeven et al. . |
| 4,659,589 | 4/1987 | Jimenez . |
| 4,687,827 | 8/1987 | Russo . |
| 4,705,820 | 11/1987 | Wang et al. . |
| 4,711,241 | 12/1987 | Lehmann . |
| 4,740,534 | 4/1988 | Matsuda et al. . |
| 4,746,544 | 5/1988 | Hogen-Esch . |
| 4,788,979 | 12/1988 | Jarrett et al. . |
| 5,007,922 | 4/1991 | Chen et al. . |
| 5,059,213 | 10/1991 | Chesterfield et al. ............. 606/228 |

FOREIGN PATENT DOCUMENTS

| | | |
|---|---|---|
| 0879582 | 2/1980 | Belgium . |
| 0170608 | 5/1986 | European Pat. Off. . |
| 0331503 | 3/1989 | European Pat. Off. . |
| 0420410 | 4/1991 | European Pat. Off. . |
| 0428253 | 5/1991 | European Pat. Off. . |
| 1579776 | 5/1969 | France . |
| 0835745 | 5/1960 | United Kingdom . |
| 2036812 | 7/1980 | United Kingdom . |
| 2071678 | 9/1981 | United Kingdom . |
| 2142945 | 1/1985 | United Kingdom . |

OTHER PUBLICATIONS

Loctite Corporation, Formula No. 18104, Feb., 1988.

*Primary Examiner*—Gary Jackson

[57] ABSTRACT

A multifilament surgical suture has an end portion tipped with cyanoacrylate resin. The suture can also include filling agents and lubricants which are incorporated into the suture prior to the suture being tipped. A typical filling agent is glycerol. A typical lubricant includes a copolymer of glycolide and lactide. Tipping is accomplished by passing a portion of the suture through a mist of monomeric cyanoacrylate resin and allowing the resin to harden by curing. The tipped portion may then be cut to create a tipped end for insertion into a surgical needle.

9 Claims, 13 Drawing Sheets

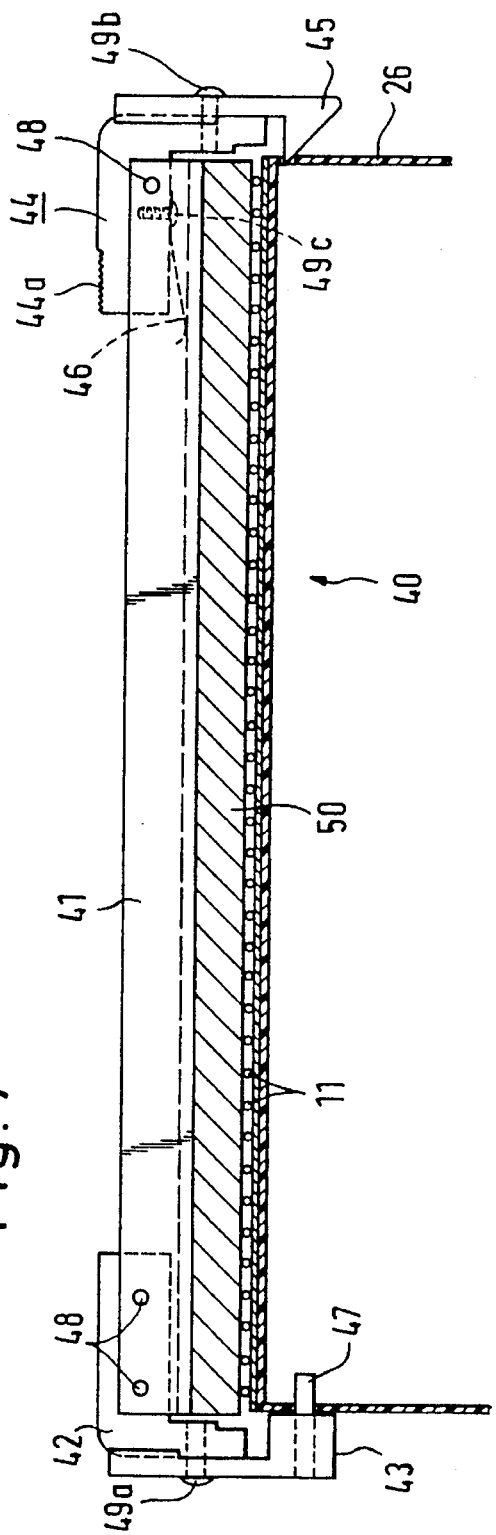

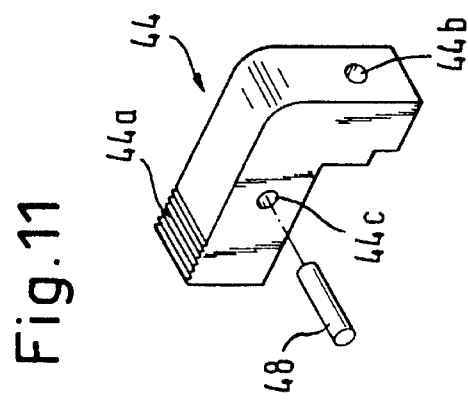
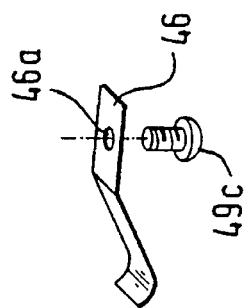
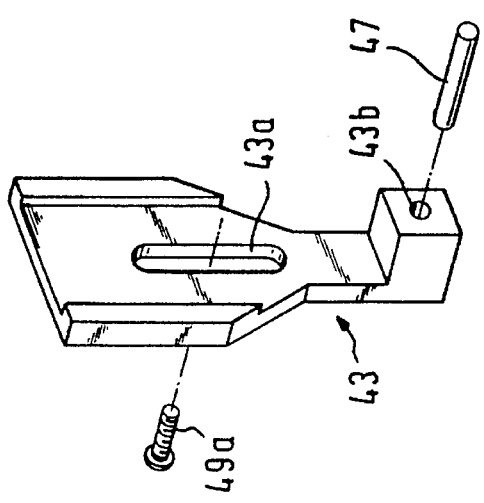
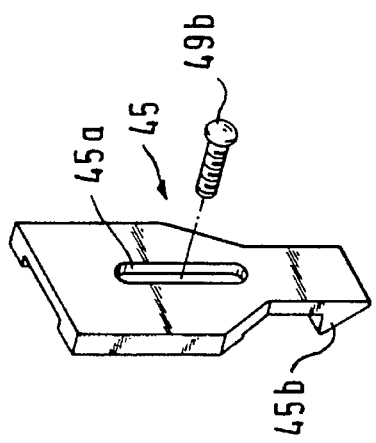
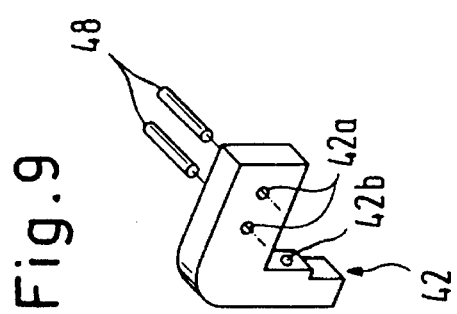

TIPPED MULTIFILAMENT SURGICAL SUTURE

This is a divisional of U.S. application Ser. No. 08/122, 072 filed Sep. 14, 1993, now U.S. Pat. No. 5,425,746, which is a divisional of U.S. application Ser. No. 08/007,361 filed Jan. 21, 1993 now U.S. Pat. No. 5,269,808, which is a continuation of U.S. application Ser. No. 07/626,995 filed Dec. 13, 1990, now abandoned.

BACKGROUND OF THE INVENTION

1. Field of the Invention

This invention relates to a tipped surgical suture and a method and apparatus for making same and a combined tipped suture and surgical needle. In particular, it relates to a cyanoacrylate tipping agent for braided sutures to prevent brooming and to increase stiffness, thereby facilitating attachment of the suture to a surgical needle.

2. Background of the Art

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acid.

Needle-suture combinations fall into two general classes: standard, or non-detachable, needle attachment and removable, or detachable, needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the United States Pharmacopoeia (USP). As to detachable needles, the United States Pharmacopoeia prescribes minimum individual pull-out forces and minimum average pull-out forces as measured for five needle-suture combinations. The minimum pull-out forces for both standard and removable needle-suture attachment set forth in the United States Pharmacopoeia are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665, 216), inclusion of protruding teeth within the axial bore to grasp an inserted suture (U.S Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one form the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 related to a flexible composite suture having a tandem linkage. The needle is secured to a flexible suture leader manufactured from a readily sterilizable plastic such as nylon, linear polyethylene, isostatic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a steel suture, e.g., monofilament stainless steel.

U.S. Pat. No. 3,918,455 describes a needle-suture attachment wherein a hollow suture portion is secured to the shank end of a needle which is of reduced cros-section as compared to the remainder of the needle.

Additional patents which describe the use of tubing to effect suture-needle attachment include U.S. Pat. Nos. 4,672, 734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

In addition to the needle-suture constructions of the aforedescribed pull-out variety, it is known from U.S. Pat. No. 4,805,292 to provide a needle-suture combination in which a suture cutting edge is formed at the shank end of the needle. However, the combined needle-suture device of U.S. Pat. No. 4,805,292, like others described above, possesses a suture tip-receiving axial bore, or recess, formed in the butt end of the needle and as such is subject to the disadvantages recounted above which are associated with a needle possessing an axial bore.

Insertion of sutures into a hole, recess or tube for attachment to surgical needles presents problems peculiar to suture needle combinations. Braided multifilament sutures in particular are difficult to insert into the very small aperture of a surgical needle: unless modified, they are too limp for the suture tip to be controlled for insertion and they have a tendency to "broom", i.e., the filaments have a tendency to flare out at the cut end so that the diameter of the cut end exceeds the diameter of the needle hole. Various techniques have been employed to modify sutures to overcome the problems of limpness and brooming. One known method employs a tipping agent, which is a material used to coat the suture to stiffen the filaments and adhere them together.

Typically, a suture to be tipped is first placed under tension to reduce slack so that the suture may be maintained in a predetermined position on a frame or rack or other suture holding device. Optionally, the tension may be such as to reduce the diameter of the suture. See Canadian Patent No. 1,009,532. The suture is then dipped into the tipping solution and allowed to dry while under tension. The sutures are then dried, such as by being warmed in a drying oven at about 225° F. for about 10 minutes. After drying the sutures can be cut and released from tension. The process results in a tipped end on each side of a cut. Where tension has optionally been employed to reduce the suture diameter, release of said tension will allow the suture to expand to its original diameter except at the tipped end portion. This can facilitate insertion of the end into a needle.

Tipping agents may be dissolved in solvents to form dipping solutions. By way of example, Mariotte mixture is a dipping solution comprising nylon dissolved in isopropyl alcohol. Other polymers and solvents may also be used. Gould mixture is a dipping solution comprising nylon dissolved in methanol. At least one major manufacturer of surgical needles recommends use of Mariotte mixture or Gould mixture for tipping sutures. A multitude of other tipping agents, including polymers and solvents, have been proposed. For example McGregor U.S. Pat. No. 3,890,975 discloses coating the suture with a binding resin or adhesive. The composition may be any non-toxic adhesive composition, either organic, inorganic or a hybrid. Suitable organic materials are such natural products as starch, dextrin, asphalt, animal and vegetable proteins, natural rubber, shellac, semi-synthetic products such as cellulose nitrate and the other cellulosics, polyamides derived from dimer acids, castor-oil based polyurethanes; such well-known synthetic resins as vinyl-type addition polymers, both resins and elastomers; polyvinyl acetate, polyvinyl alcohol, acrylics, unsaturated polyesters, butadiene/acrylonitrile, butadiene/styrene, neoprene, butyl rubber, polyisobutylene; and polymers formed by condensation and other step-wise mechanisms, i.e., epoxies, polyurethanes, polysulfide rubbers, and the reaction products of formaldehyde with phenol, resorcinol, urea, and melamine. McGregor states that particularly preferred bonding compositions are epoxide resins and polyester resins.

Schmitt U.S. Pat. No. 3,736,646 discloses that it is known to tip braided sutures by dipping the end of the suture in a plastic such as a solution in isopropyl alcohol. Schmitt suggests that for absorbable sutures an absorbable tipping agent is desirable, and proposes that a copolymer of lactic and glycolic acid dissolved in a suitable organic solvent, such as xylene or toluene, be applied to tip the suture.

Nichols U.S. Pat. No. 2,734,506 discloses a dipping solution of polymers of methacrylic acid esters in an organic solvent such as toluene, xylene acetone, ethyl acetate, methylethyl ketone, or naphtha.

Shepherd et al. U.S. Pat. No. 3,849,185 discloses the use of an acrylic casting syrup as a tipping agent, the syrup being fully polymerized after being applied to the suture.

In addition, paraffin/hexane solution (10% paraffin) has been used as a suture coating agent as well as Arrochem (TM), a nylon resin plus methanol composition manufactured by ArroChem, Inc. of 201 Westland Farm Road, Mt. Holly, NC 28120, and SILASTIC (TM) Medical Adhesive (a silicon elastomer composition manufactured by Dow Corning Co.

Although dipped sutures prepared in accordance with the above procedures may have been used successfully, there are several drawbacks with the use of tipping solutions. The main problems relate to tipping consistency and process control. Non-uniform solvent evaporation, which may be caused by variations in the solvent, oven temperature and heating time can result in inconsistent tipping. Furthermore, the dried residue of polymer left after evaporation can flake off or develop cracks.

Another method which has been employed for treating sutures involves melt fusion, as described in U.S. Pat. No. 4,832,025, issued to Coates. The suture is . heated to a temperature at least high enough to "melt fuse" a portion of the outer filaments of the suture. According to Coates, such temperature is typically about 260° C. to 300° C. (500° F. to 572° F). Exposure of synthetic sutures to such extreme temperatures melt fuses the filaments, and the melt fused suture portion stiffens upon cooling. Melting of the filaments has the effect of holding the filaments together when the suture is cut. It also causes stiffening of the suture which facilitates insertion of the suture end into the drilled hole of a needle. However, the melt fusion of suture has significant drawbacks.

Firstly, the melt fusion of filaments weakens the suture, whose tensile strength is degraded in proportion to the extent of melt fusion.

Secondly, melt fusion causes an irreversible change in the filaments which result in permanent stiffening and permanent loss of tensile strength.

Thirdly, with the extreme temperatures disclosed by Coates for melt fusion an inconveniently short heating cycle is required. For example, for a size 3/0 silicone coated polyester suture heated to between 260° C. to 300° C. in a 4 mm. diameter eating tunnel, the heating time is no more than about 3 seconds. Such short heating times make it difficult to control the process and leads to inconsistencies and variations in the melt fused tipping process.

A further consideration pertinent to suture tipping is that sutures are often prepared with lubricant coatings such as silicone or fatty acid salts in order to increase lubricity and to improve "tie-down" performance, i.e., the ease of sliding a knot down the suture into place. Such lubricant coatings typically are incompatible with the materials and methods currently employed for tipping sutures. In particular, prior known tipping agents do not adhere well to lubricant coated sutures, which may result in inconsistent tipping or an undesirable reduction of suture-needle pull out force. The melt fusing method of tipping may destroy the lubricant coating or render it less effective in areas away from the needle.

A method of and apparatus for tipping surgical sutures has been discovered which may be used to tip both uncoated and coated sutures and which provides superior stiffening of the suture for insertion into an opening to attach the suture to a needle.

SUMMARY OF THE INVENTION

A surgical suture tipped with cyanoacrylate and a process for tipping with cyanoacrylate are disclosed. In addition, a method and apparatus are provided herein for handling and tipping a surgical suture.

In the preferred embodiment a suture is wound around a drum while its diameter is continuously monitored in the x and y directions, with the tension on the suture continuously being adjusted to consistently control the diameter of the suture as it is wound onto the drum. The drum is then placed in an apparatus which passes selected portions of the suture through a mist of cyanoacrylate tipping agent generated by sonic or ultrasonic atomization. The tipping agent quickly cures as it polymerizes in response to ambient residual moisture to stiffen the coated portion of the suture. The coated portion of the suture may be cut to create at least one tipped end for insertion into a surgical needle. To assure consistent repeated processing the atomization apparatus is flushed before and after each cycle with nitrogen in order to prevent curing of the cyanoacrylate in the apparatus, which would undesirably interfere with proper operation of apparatus. Advantageously, cyanoacrylate tipping in accordance with the invention can be used effectively to tip all types of sutures, including filled sutures and sutures coated with lubricants and the like.

BRIEF DESCRIPTION OF THE DRAWINGS

FIG. 7 is a side view of the suture retaining clamp of the present invention.

FIG. 8 is a perspective view of the main support of the suture clamp.

FIG. 9 is a perspective view of the dowel arm support of the present invention.

FIG. 10 is a perspective view of the dowel arm of the present invention.

FIG. 11 is a perspective view of the rocker clamp support of the present invention.

FIG. 12 is a perspective view of the rocker clamp of the present invention.

FIG. 13 is a perspective view of the rocker spring of the present invention.

DETAILED DESCRIPTION OF PREFERRED EMBODIMENTS

Figure 1:
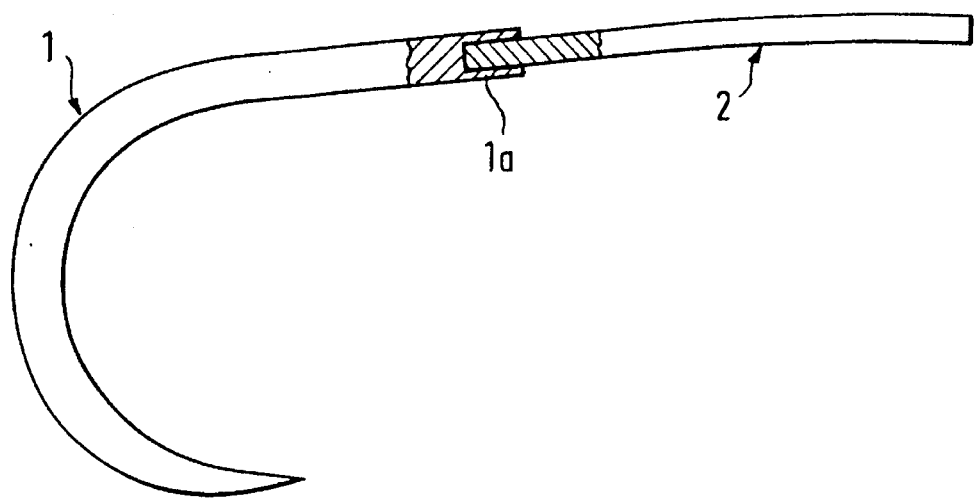
FIG. 1 is a partially cutaway side view illustrating a surgical needle and suture combination.

The present invention is generally directed to tipping surgical sutures with cyanoacrylate in order to stiffen the suture tip and, as to multifilament sutures, prevent brooming. Tipping the suture with cyanoacrylate facilitates insertion of the suture tip into an opening for attachment to a suture. Advantageously, the cyanoacrylate tipping is compatible with a broad range of sutures and coatings, and a novel method and apparatus have been developed for applying cyanoacrylate to sutures in an atomized spray. Because the cyanoacrylate tipping agent and process are applicable to a wide range of materials and needle suture attachment methods, suture constructions and general methods of tipping sutures will be discussed prior to discussing the preferred apparatus for spray tipping.

THE SUTURE

The present invention is primarily directed to the treatment of braided surgical sutures. The term "braid" means a substantially symmetrical strand formed by crossing a number (at least three) of individual strands composed of one or more filaments diagonally in such manner that each strand passes alternatively over and under one or more of the others. The braid may be of traditional tubular braid construction or spiroid braid construction and may include a core section composed of one or more filaments around which the braid is externally fabricated.

The braided suture can be fabricated from a wide variety of natural and synthetic fibrous materials such as any of those heretofore disclosed for the construction of sutures. Such materials include non-absorbable as well as partially and fully bio-absorbable (i.e., resorbable) natural and synthetic fiber-forming polymers. Non-absorbable materials which are suitable for fabricating braided sutures include silk, polyamides, polyesters such as polyethylene terephthalate, polyacrylonitrile, polyethylene, polypropylene, silk cotton, linen, etc. Carbon fibers, steel fibers and other biologically acceptable inorganic fibrous materials can also be employed. Bio-absorbable sutures may be fabricated from natural collagenous material or synthetic resins including those derived from glycolic acid, glycolide, lactic acid, lactide, dioxanone, polycaprolactone, epsilon-caprolactone, trimethylene carbonate, etc., and various combinations of these and related monomers. Sutures prepared from resins of this type are known in the art.

Braided multifilament sutures typically are coated with one or more coating compositions to improve functional properties such as surface lubricity and knot tie-down behavior. A variety of suture coating compositions proposed for either or both of these purposes are well known in the art, e.g., those disclosed in U.S. Pat. Nos. 3,867,190; 3,942,532; 4,047,533; 4,452,973; 4,624,256; 4,649,920; 4,716,203; and 4,826,945.

A preferred lubricant coating is a bioabsorbable coating composition obtained by copolymerizing in accordance with known procedures (1) a polyether glycol selected from the group consisting of relatively low molecular weight polyalkylene glycol, e.g., one corresponding to the general formula HO(RO),H wherein R is an alkylene group of from 2–4 carbon atoms and y is an integer of from about 100–350, and polyethylene oxide-polypropylene oxide block copolymer, e.g., one corresponding to the general formula $H(OCH_2CH_2)_x(OC_3H_6)_y(OCH_2CH_2)_zOH$ wherein x is an integer of from about 45–90, y is an integer of from about 60–85 and z is an integer of from about 45–90 with (2) a mixture of lactide monomer and glycolide monomer or a preformed copolymer of lactide an glycolide, the weight ratio of (1) to (2) preferably ranging from about 4:1 to about 1:4 and more preferably from about 2:1 to about 1:2. The ratio of lactide to glycolide in the monomer mixture or in the copolymer of these monomers preferably varies from. about 65–90 mole percent lactide and 10–35 mole percent glycolide. Polyether glycols having molecular weights of about 3,500–25,000 and preferably from about 4,000–10,000 and polyethylene oxide-polypropylene oxide block copolymers having molecular weights of from about 4,000–10,000 and preferably from about 7,500 to about 9,000, e.g., those disclosed in U.S. Pat. Nos. 2,674,619, 3,036,118, 4,043,344 and 4,047,533 and commercially available as they Pluronics (BASF-Wyandotte). Where preformed copolymers of lactide and glycolide are employed in preparing the bioabsorbable coating compositions, they may be prepared as described in U.S. Pat. No. 4,523,591.

The amounts of bioabsorbable coating composition to be applied to the suture, e.g., by coating, dipping, spraying or other appropriate techniques, will vary depending upon the specific construction of the suture, its size and the material of its construction. In general, the coating composition applied to an unfilled suture will constitute from about 1.0 to about 3.0 percent by weight of the coated suture, but the amount of coating add on may range from as little as about 0.5 percent, by weight, to as much as 4.0 percent or higher. For a preferred filled (i.e. containing a storage stabilizing agent) braided suture, amounts of coating composition will generally vary from about 0.5% to about 2.0% with as little as 0.2% to as much as 3.0%. As a practical matter and for reasons of economy and general performance, it is generally preferred to apply the minimum amount of coating composition consistent with good surface lubricity and/or knot tie-down characteristics and this level of coating add on is readily determined experimentally for any particular suture.

Recently it has been proposed to also apply to an absorbable braided suture a storage stabilizing amount of a filler material containing at least one water soluble liquid polyhydroxy compound and/or ester thereof. In addition to laving an enhanced degree of storage stability, a braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances, they can be used as vehicles to deliver such substances to a wound or surgical site at the time the suture is introduced into the body.

The useful .storage stability agents are generally selected from the water soluble, liquid polyhydroxy compounds and/or esters of such compounds, preferably those having no appreciable toxicity for the body at the levels present. The expression "liquid polyhydroxy compound" contemplates those polyhydroxy compounds which in the essentially pure state are liquids, as opposed to solids, at or about ambient temperature, e.g., at from about 15° C. to about 40° C. The preferred polyhydroxy compounds possess up to about 12 carbon atoms and where the esters are concerned, are preferably the monoesters and diesters. Among the specific storage stabilizing agents which can be used with generally good results are glycerol and its mono-and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of storage stabilizing agents, e.g., sorbitol dissolved in glycerol, glycerol combined with monoacetin and/or diacetin, etc., are also useful.

To prevent or minimize run-off or separation of the storage stabilizing agent from the suture, a tendency to which relatively low viscosity compounds such as glycerol are especially prone, it can be advantageous to combine the agent with a thickener. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015 referred to above, polysaccharide gums such as guar, xanthan, and the like, gelatin, collagen, etc. An especially preferred class of thickeners are the saturated aliphatic hydroxycarboxylic acids of up to about 6 carbon atoms and the alkali metal and alkaline earth metal salts and hydrates thereof. Specific examples of such compounds include salts of lactic acid such as calcium lactate and potassium lactate, sodium lactate, salts of glycolic acid such as calcium glycolate, potassium glycolate and sodium glycolate, sales of 3-hydroxy propanoic acid such as the calcium, potassium and sodium salts thereof, salts of 3-hydroxybutanoic acid such as calcium, potassium and sodium salts thereof, and the like. As stated hereinabove, hydrates of these compounds Call also be used. Calcium lactate, especially calcium lactate pentahydrate, is a particularly preferred thickener.

When a thickener is utilized, it will be incorporated in the filling composition in at least that amount required to increase the overall viscosity of the storage stabilizing agent to the point where the agent no longer readily drains away from the suture in a relatively short period. In the case of a preferred storage stabilizing agent-thickener combination, namely, glycerol and calcium lactate, the weight ratio of glycerol to calcium lactate can vary from about 1:1 to about 10:1 and preferably is from about 6:1 to 8:1.

If necessary or desirable, the storage stabilizing agent together with optional thickener can be dissolved in any suitable non-aqueous solvent or combination of solvents prior to use. To be suitable, the solvent must (1) be miscible with the storage stabilizing agent and optional thickener, if present (2) have a sufficiently high vapor pressure to be readily removed by evaporation, (3) not appreciably affect the integrity of the suture and (4) be capable of wetting the surface of the suture. Applying these criteria to a preferred storage stabilizing agent, glycerol, advantageously in admixture with a preferred thickener, calcium lactate, lower alcohols such as methanol and ethanol are entirely suitable solvent carriers. When a solvent is utilized in the preparation of the stabilizing agent, e.g., methanol, such solvent can be employed in amounts providing a solution concentration of from about 20% to about 50%, preferably about 30% to about 45%, by weight of the storage stabilizing agent including any optional thickener.

As stated, a braided suture may be impregnated with one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the braided suture of the present invention. Such materials include any of several human Growth factors (HGFs), magainin, tissue or kidney plasminogen activator to cause thrombosis, superoxide dismutase ot scavenge tissue damaging free radicals, tumor necrosis factor for cancer therapy, colony stimulating factor, interferon, interleukin-2 or other lymphokine to enhance the immune system, and so forth.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See e.g., Tomlinson (Ciba-Geigy Pharmaceuticals, West Sussex, U.LK.), "Selective Delivery and Targeting of Therapeutic Proteins", a paper presented at a symposium held Jun. 12–14, 1989 in Boston, MA, the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of Biogrowth, Inc., Richmond, CA presented at the aforementioned symposium, the contents of said paper being incorporated by reference herein. The HIGFs can also be incorporated in liposomes to provide for their release over an extended period. Lactate ion can be present to augment the wound healing activity of the HIGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

CYANOACRYLATE TIPPING

As stated previously, prior known tipping methodologies are not fully compatible with a suture or its coatings, fillers, therapeutic agents, antimicrobial agents and/or biologically active materials, either because the tipping agent will not adhere properly or because the methodology (such as melt fusing) results in deterioration of the suture, its coatings, additives, and fillers.

The suture tipping agent and method of the present invention are compatible with and may be used on any type of surgical suture including multifilament bioabsorbable or non-bioabsorbable sutures. Advantageously, the tipping agent and method of the invention are applicable to all types of multifilament braided sutures, including those which contain one or more fillers, coatings, etc.

In practice, a segment of the suture is selected for tipping and may be of any length appropriate for inserting a suture end cut from such segment into an opening, such as the barrel end of a surgical needle, to facilitate attachment of the suture to the needle.

Typically the suture is placed under sufficient tension to take up slack. Additional tension may be applied to reduce the suture diameter, if desired, to result in a tipped section of reduced diameter relative to the remainder of the suture.

A stiffening or "tipping" agent is then applied to the selected segment of suture. The stiffening agent is a cyanoacrylate monomer such as methyl 2-cyanoacrylate, or ethyl 2-cyanoacrylate. The preferred cyanoacrylate is available under the name LOCTITE(TM) Medical Device Adhesive 18014 and is available from the Loctite Corporation, 705 N. Mountain Road, Newington, CT 06111. The preferred Loctite Medical Device Adhesive is a moisture activated polymer which comprises 99+% ethyl cyanoacrylate and small amounts of hydroquinone and organic anhydride. It has a specific gravity of 1.05, and a boiling point greater than 300° F. The cyanoacrylate monomer may be applied in a variety of ways, such as dipping or brushing and preferably is applied by spraying, as described below. Upon contact with the suture, the residual moisture of the suture and surrounding environment catalyzes the polymerization of the cyanoacrylate almost instantly. The polymerized cyanoacrylate stiffens the segment of the suture by coating the individual filaments of the suture with a relatively stiff coating, and, because the cyanoacrylate is an adhesive, the individual filaments are bonded together to prevent brooming. A further advantage of the ethyl cyanoacrylate tipping agent is that it is bioabsorbable and will not leave a permanent residue in body tissue. Because the cyanoacrylate polymerizes almost instantly, the tipping agent is stiffened immediately without any additional drying or curing steps. This has the added advantage of reducing processing steps and accompanying handling and equipment requirements. In the preferred spray tipping process, polymerization is substantially complete by the end of the apparatus cycle and the tipped suture may be further processed without delay.

The next step is cutting the stiffened segment to create at least one "tipped" end for connecting to the end of a surgical needle. Two tipped ends of the suture may be desirable for attaching a needle to each end of the suture to provide a so-called double armed suture. The coated segment may be cut with scissors, a razor blade, or by a knife edge moving transverse to the direction of the tipped suture segment, or by any other suitable means.

SUTURE-NEEDLE ATTACHMENT

The tipped end is now ready to be connected to the surgical needle.

One method of connection, illustrated in FIG. 1, requires a needle 1 with a barrel end having an axial aperture 1a. The tipped end of suture 2 is inserted into the aperture 1a and the end of the needle may then be swaged, crimped or otherwise constricted to grip and hold the suture, either permanently or with a pull-out force defined by U.S.P. for detachable needles. The swage or crimp method of attachment is conventional and well known in the art.

Figure 2:
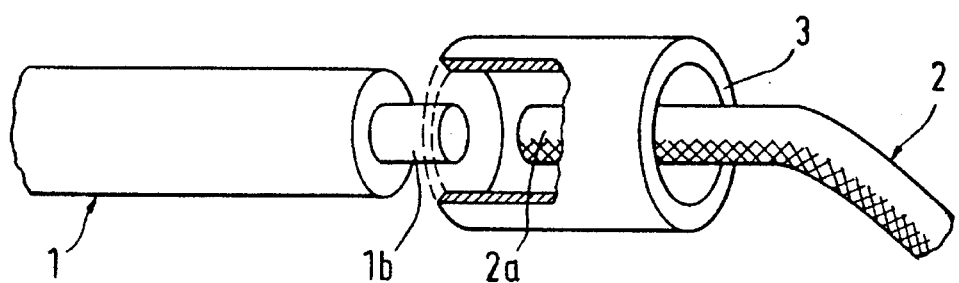
FIG. 2 is an exploded perspective view illustrating a surgical needle in conjunction with a suture.

Another method of attaching the suture to the needle is illustrated in FIG. 2 wherein the barrel end of the needle 1 has a cylindrical portion 1b of lesser diameter than the needle and extending axially from the needle 1. The "tipped" or stiffened end 2a of suture 2 is positioned adjacent portion 1b and extends axially through the bore of a tube 3, which is positioned around the junction of tipped end 2a and needle portion 1b. Tube 3 is made of a material capable of shrinking or undergoing contraction upon application of energy, e.g., heat. Suitable materials include "memory based metals," e.g., nickel-iron-titanium mixtures, or copper based materials, as are well known in the art (see, e.g., U.S. Pat. Nos.

3,759,552, 3,801,954, 4,198,081 and 4,733,680), and shrinkable plastic materials, such as polyvinylidene fluoride materials available from Raychem Corporation, Menlo Park, Calif., under the tradename Kynar. One such polyvinylidene fluoride material available from Raychem Corporation is RT-850. In the case of shrinkable plastic materials, the tubing typically is extruded such that the inner diameter is less than the final desired diameter, i.e., the inner diameter of the tubing after energy application in the attachment method of the present invention. Thereafter, the extruded tubing is expanded radially outward through radial expansion means to provide a tubing or expanded inner diameter. Such plastic tubing is thus adapted to shrink or "recover" to its original extruded inner diameter in response to the application of a predetermined amount of energy. Suitable energy sources to accomplish shrinking of tubing 3 include heat (convective or conductive), radiation, microwave energy, etc.

Figure 3:
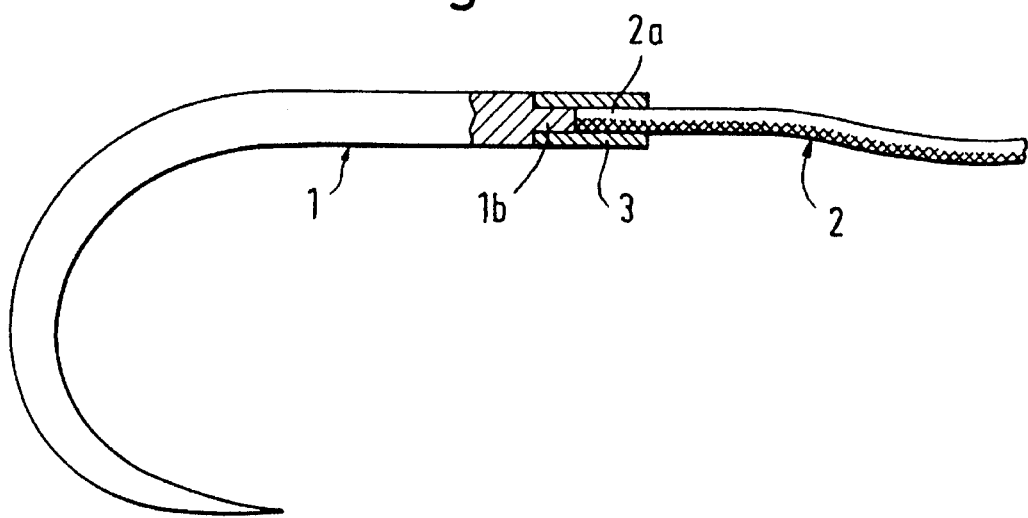
FIG. 3 is a partially cutaway side view illustrating a surgical needle in combination with a suture.

Tube 3 is then subjected to energy, preferably consisting of heat, in order to cause shrinkage or contraction of the tube such that the inner surface of the tube bore grips both the needle portion 1a and the suture end 2a in the vicinity of the joint as shown in FIG. 3. Alternatively, the tube may be attached to the needle and suture sequentially, such as by first applying localized energy to shrink the tube onto the needle shank and thereafter applying energy to the remainder of the tube to shrink the tube into the suture tip. Variations in the needle shank, such as tapering, contouring or ribbing, may be used to increase gripping force of the tube to the needle. Similarly, the relative gripping force of the tube on the needle shank and suture may be varied by varying the length of the tube section contacting each of the needle shank and suture. In addition, tube 3 preferably is configured and dimensioned such that when it is contracted the outer surface of the tube is substantially flush or even with the outer surface of the needle. The gripping force of the shrinkable tube 3 is sufficient to maintain the minimum required pull out force for the suture, and may be adjusted to provide either permanently attached or detachable suture needles. It has been found that sutures, particularly coated and filled sutures, tipped in accordance with the method of the present invention have significantly higher pull out forces.

Attempts were made to tip coated sutures, such as silicone coated Dacron® braided sutures, with polyurethane and epoxy adhesives. These attempts did not result in any tipped sutures suitable for attachment to needles.

COMPARATIVE EXAMPLES 1–2

Dacron® polyester 1-0 braided sutures coated with silicone were tipped by swab application of (i) Arrochem composition; and (ii) a "hot melt" 10% paraffin/hexane solution. Sutures tipped with the 10% paraffin/hexane were further treated for 60 seconds in a heating apparatus set at 315° F. The 10% paraffin/hexane solution was difficult to work with since it had to be maintained at about 130° F. with constant stirring in order to maintain the paraffin in solution. The tipped sutures were swaged to needles in a conventional manner and pull-out force in both cases was measured to be about 0.05 kg.

COMPARATIVE EXAMPLE 3

In an attempt to improve on the results of Comparative Examples 1–2, Dacron® polyester 1-0 braided sutures were placed in toluene and brought to temperature of 80°–82° C. for ten minutes. The total dwell time in toluene was approximately 20 minutes. The washed sutures were tipped with 10% paraffin/hexane by swab application and heated to 315° F. for 60 seconds. The maximum pull-off forces were approximately 0.05 kg, showing no improvement.

COMPARATIVE EXAMPLES 4–14

Dacron® polyester 1-0 braided sutures coated with silicone were ultrasonically washed for five minutes in one of isopropyl alcohol, TP10, Freon TF, hexane, xylene, and III-trichloromethane. Samples of sutures washed by each method were tipped with Arrochem solution and 10% paraffin/hexane (the paraffin/hexane tipped sutures were heated to 315° F. for 60 seconds, as before), resulting in twelve types of differently treated and tipped sutures. The tipped sutures were swaged to needles and the pull-out force was measured. The pull-out forces of these sutures showed some improvement, having pull-out forces of about 1.5 kg, but still did not achieve reliably high pull-out forces.

COMPARATIVE EXAMPLES 15–16

Silicone coated Dacron® polyester 1-0 braided sutures were wound on a paddle and soaked for five minutes in a 5% Mariotte mixture solution (50 grams nylon in 946 ml. isopropyl alcohol and 150 ml. water). Thereafter, the sutures were heated for 60 seconds at 315° F. and, after cooling, Arrochem solution was applied over the tip previously treated with Mariotte mixture. No improvement in pull out force was obtained, and the extended exposure to Mariotte mixture was observed to have detrimental effects on the suture braid.

The above procedure was repeated using a 10 minute soak in Mariotte mixture followed by heat treating for 10 minutes in an oven at 225° F, followed by tipping with Arrochem composition. No improvement in pull-out force was observed when these sutures were attached to needles.

COMPARATIVE EXAMPLE 17

Silicone coated Dacron® polyester 1-0 braided sutures were ultrasonically washed for 5 minutes in toluene and tipped with 10% paraffin/hexane solution by swab application. The pull-off force met U.S.P. minimums, e.g. 0.45 kg, but was still insufficient.

COMPARATIVE EXAMPLES 18–29

Silicone coated Dacron® polyester 1-0 braided sutures were ultrasonically washed for 10 minutes in a variety of different washing solutions, tipped by soaking for 5 minutes in either Arrochem or 5% Mariotte mixture, and attached to needles. The results are listed below in Table I.

TABLE I

| | Cleaning Solution | Tipping Agent | Pull-Off Force (kg) |
|---|---|---|---|
| 18. | Isopropyl alcohol | Arrochem | 0.05–1.0 |
| 19. | Isopropyl alcohol | Paraffin/Hexane | 0.05–1.0 |
| 20. | Freon T-F | Arrochem | 0.05–1.0 |
| 21. | Freon T-F | Paraffin/Hexane | 0.05–1.0 |
| 22. | Freon TP 10 | Arrochem | 0.05–1.0 |
| 23. | Freon TP 10 | Paraffin/Hexane | 0.05–1.0 |
| 24. | Trichloroethylene | Arrochem | 0.05–1.0 |
| 25. | Trichloroethylene | Paraffin/Hexane | 0.05–1.0 |
| 26. | Xylene | Arrochem | 0.08–1.3 |
| 27. | Xylene | Paraffin/Hexane | 0.08–1.3 |
| 28. | Hexane | Arrochem | 0.08–1.3 |
| 29. | Hexane | Paraffin/Hexane | 0.08–1.3 |

COMPARATIVE EXAMPLES 30–33

Braided Dacron® polyester size 1-0 braided sutures were ultrasonically washed in a toluene bath for 20 minutes. After solvent cleaning the sutures were tipped by soaking for 5 minutes in one of (i) 10% Silastic Medical Adhesive in hexane; (ii) 10% paraffin/hexane; (iii) Arrochem solution; or (iv) Mariotte mixture. All the tipped sutures were post-tipped at 315° F. for 60 seconds. The tipped ends were cut and inserted into surgical needles, the needles were swaged, and the pull out forces were measured. The results are set forth in Table II.

TABLE II

| Pull-out forces for Dacron ® polyester 1-0 braided sutures ultrasonically cleaned in toluene for 20 minutes. | |
|---|---|
| Tipping Agent | Pull-Out Force kg |
| 30. Silastic/Hexane | 1.0–1.8 |
| 31. Paraffin/Hexane | 1.0–1.6 |
| 32. Arrochem | 1.3–1.8 |
| 33. Mariotte Mixture | 1.8–2.5 |

From the foregoing it would appear that ultrasonic washing in toluene for 20 minutes prior to tipping with a conventional agent might lead to acceptable results. Unfortunately, however, toluene is an undesirable material due to its toxicity and the harsh effects on the suture material.

EXAMPLES 1–6

Samples were selected for testing of (i) size O braided synthetic absorbable sutures made from 90% glycolide, 10% lactide coated with a glycolide/lactide/polyethylene oxide mixture, and filled with glycerin/calcium lactate; and (ii) braided nylon (non-bioabsorbable) sutures coated with silicone lubricant. Selected segments of the sutures were tipped with Loctite Selected segments of the sutures were tipped with Loctite Adhesive 18014, which was allowed to fully polymerize. The suture segments were cut to create tipped ends which were then inserted into a drilled hole in the barrel end of surgical needles. The needles were then swaged by a) double hit swaging, b) split-ring, and c) clover leaf dies, and pull out forces for each type of attachment were measured. Further information regarding split-ring and clover leaf swaging may be found in U.S. Pat. application Ser. Nos. 07/431,303 and 07/431,306 both filed Nov. 3, 1989. The test results are set forth in Tables III, IV and V below.

TABLE III

| | | Cyanoacrylate-Tipped Sutures Conventional Double-Hit Swaging | | | | | |
|---|---|---|---|---|---|---|---|
| | | PRE-STERILIZATION PULL-OUT FORCE | | | POST-STERILIZATION PULL-OUT FORCE | | |
| SUTURE | SIZE | SAMPLES | AVG. | RANGE | SAMPLES | AVG. | RANGE |
| 1. Synthetic Absorbable* | 0 | n = 5 | 2.6 kgs. | — | n = 5 | 2.9 kgs. | — |
| 2. Braided Nylon** | 0 | n = 10 | 1.8 kgs. | — | n = 10 | 1.8 kgs. | — |

TABLE IV

| | | Cyanoacrylate-Tipped Sutures Split Ring Swaging | | | | | |
|---|---|---|---|---|---|---|---|
| | | PRE-STERILIZATION PULL-OUT FORCE | | | POST-STERILIZATION PULL-OUT FORCE | | |
| SUTURE | SIZE | SAMPLES | AVG. | RANGE | SAMPLES | AVG. | RANGE |
| 3. Synthetic Absorbable* | 0 | n = 15 | 3.2 kgs. | 2.9–3.7 kgs. | n = 8 | 3.1 kgs. | 2.5–3.4 kgs. |
| 4. Braided Nylon** | 0 | n = 11 | 3.3 kgs. | 1.4–7.1 kgs. | n = 15 | 2.9 kgs. | 2.4–3.2 kgs. |

TABLE V

| | | Cyanoacrylate-Tipped Sutures Clover Leaf Swaging | | | | | |
|---|---|---|---|---|---|---|---|
| | | PRE-STERILIZATION PULL-OUT FORCE | | | POST-STERILIZATION PULL-OUT FORCE | | |
| SUTURE | SIZE | SAMPLES | AVG. | RANGE | SAMPLES | AVG. | RANGE |
| 5. Synthetic Absorbable* | 0 | n = 15 | 3.5 kgs. | 2.8–4.4 kgs. | n = 15 | 3.3 kgs. | 2.5–4.1 kgs. |

TABLE V-continued

| | | Cyanoacrylate-Tipped Sutures Clover Leaf Swaging | | | | | |
|---|---|---|---|---|---|---|---|
| | | PRE-STERILIZATION PULL-OUT FORCE | | | POST-STERILIZATION PULL-OUT FORCE | | |
| SUTURE | SIZE | SAMPLES | AVG. | RANGE | SAMPLES | AVG. | RANGE |
| 6. Braided Nylon** | 0 | n = 15 | 2.9 kgs. | 1.5–3.9 kgs. | n = 15 | 3.2 kgs. | 1.9–4.1 kgs. |

*Synthetic Absorbable Sutures (90% glycolide/10% lactide) coated with with a glycolide/lactide/polyethylene oxide copolymer and filled with glycerine/calcium lactate mixture
**Braided Nylon Sutures coated with silicone lubricant.

The minimum pull out force required by the U.S. Pharmacopeia for size 0 suture is 1.5 kg Avg/0.45 kg individual. As can be seen from Tables III, IV, and V, the pull out forces for the cyanoacrylate tipped sutures exceeds the minimum USP requirements.

As can be seen from a comparison of the pull-out forces tabulated in the above examples and comparative examples, the suture tipping method of the present invention using cyanoacrylate tipping agent produces pull-out forces superior to those of methods using prior known tipping agents, particularly with respect to filled sutures and sutures coated with lubricant coatings. Remarkably, these results are attained without washing the suture prior to cyanoacrylate tipping. This is surprising since the prior known methods of using cyanoacrylates typically require the surface to be bonded to be free of oils, mold release agents, or other foreign matter in order to achieve maximum bond performance.

TIPPING APPARATUS

The following description discloses the preferred apparatus for spraying cyanoacrylate monomer onto the suture by atomization.

METHOD FOR WINDING A SUTURE

Figure 4:
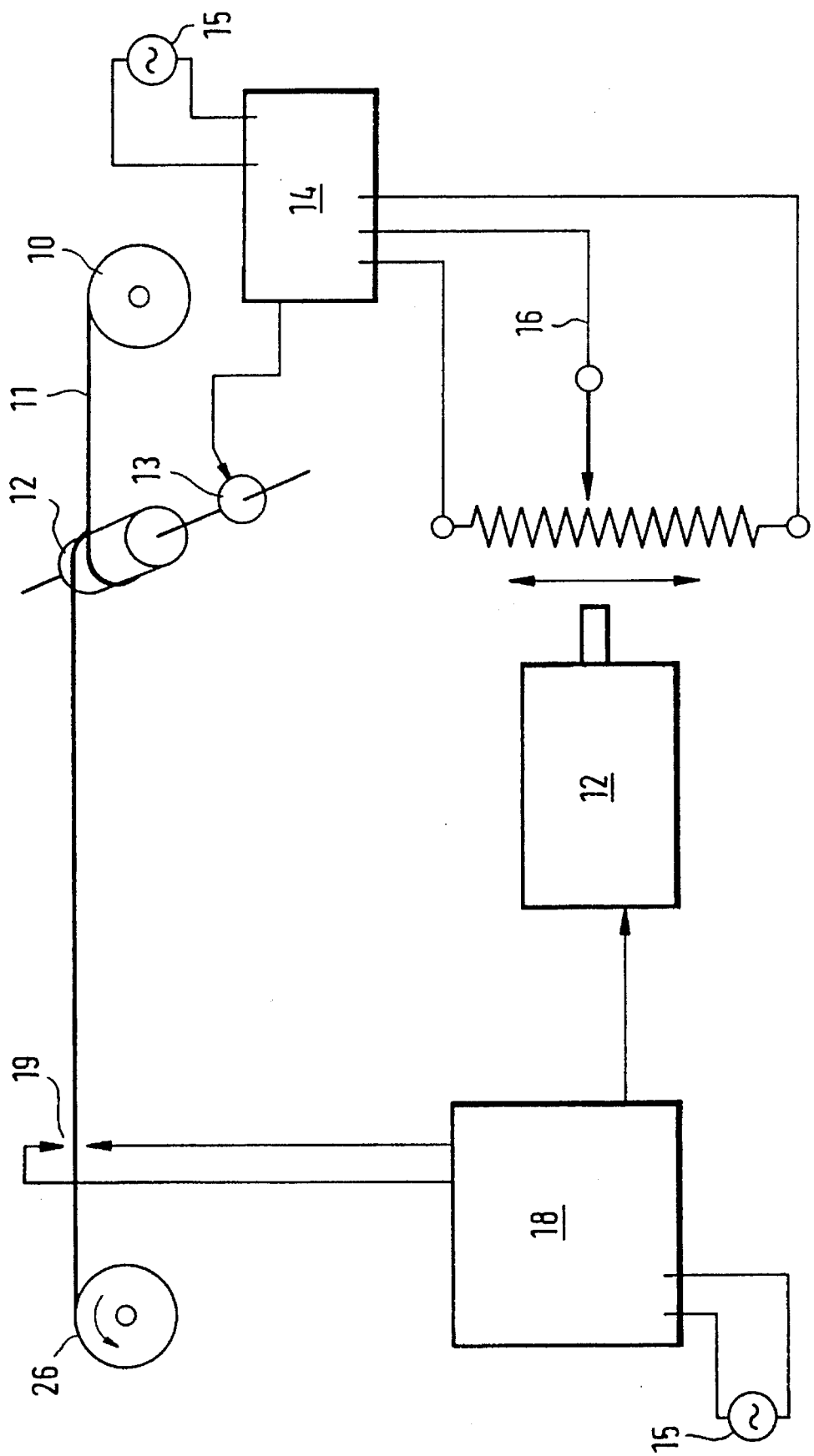
FIG. 4 is a diagrammator illustration of the suture winding system of the present invention.

To insure consistency of the diameter at the tipped portion of the suture, a method and apparatus have been developed for monitoring suture ovality and adjusting winding tension to control and, if desired, modify the suture diameter. A diagram of the system for loading sutures on a drum is illustrated in FIG. 4.

The pay off section includes a spool 10 on which suture material 11 is stored. A friction tensioning device applies drag to the outside of the spool to prevent the spool from freewheeling. The suture is guided onto a capstan 12 which is electronically controlled by means of friction clutch 13 and clutch power supply 14. The suture 11 then passes onto the drum assembly 26. Power is supplied by standard 120 volt power sources 15. When tension is applied to the suture, the suture diameter is reduced. When the clutch is relaxed, the diameter of suture material under tension expands. Based on dimensional information continuously fed to the clutch control from an x-y laser micrometer 18, the clutch applies tension to or releases the suture in order to maintain suture diameter within selected parameters.

The x-y laser micrometer 18 continuously monitors the diameter of the suture in the x and y directions, i.e. suture ovality, by means of x-y heads 19 which are oriented orthogonal to each other. The laser micrometer electronically compares the x-y measurements with preselected minimum and maximum dimensions pertaining to the particular type and size of suture. This information is employed in a negative feedback control loop whereby the clutch tension is adjusted by means of a drive motor 17 and potentiometer clutch controller 16. In the event either dimension exceeds the maximum diameter for the suture size, the clutch tension is increased in order to decrease the diameter of the suture. In the event either dimension is less than the minimum suture diameter the clutch tension is relaxed until the suture diameter is increased into the suture diameter range. The information is processed and clutch tension adjusted within milliseconds of the actual measurement to continuously adjust clutch tension.

Referring more specifically to the laser micrometer, an instrument suitable for use in the present invention is available from Zumbach Electronics Corp., 140 Kisco Avenue, Mount Kisco, N.Y. 10549 under the designation ODAC 19M, which is a microcomputer controlled measuring system having x-y heads which incorporate laser scanners.

Figure 5:
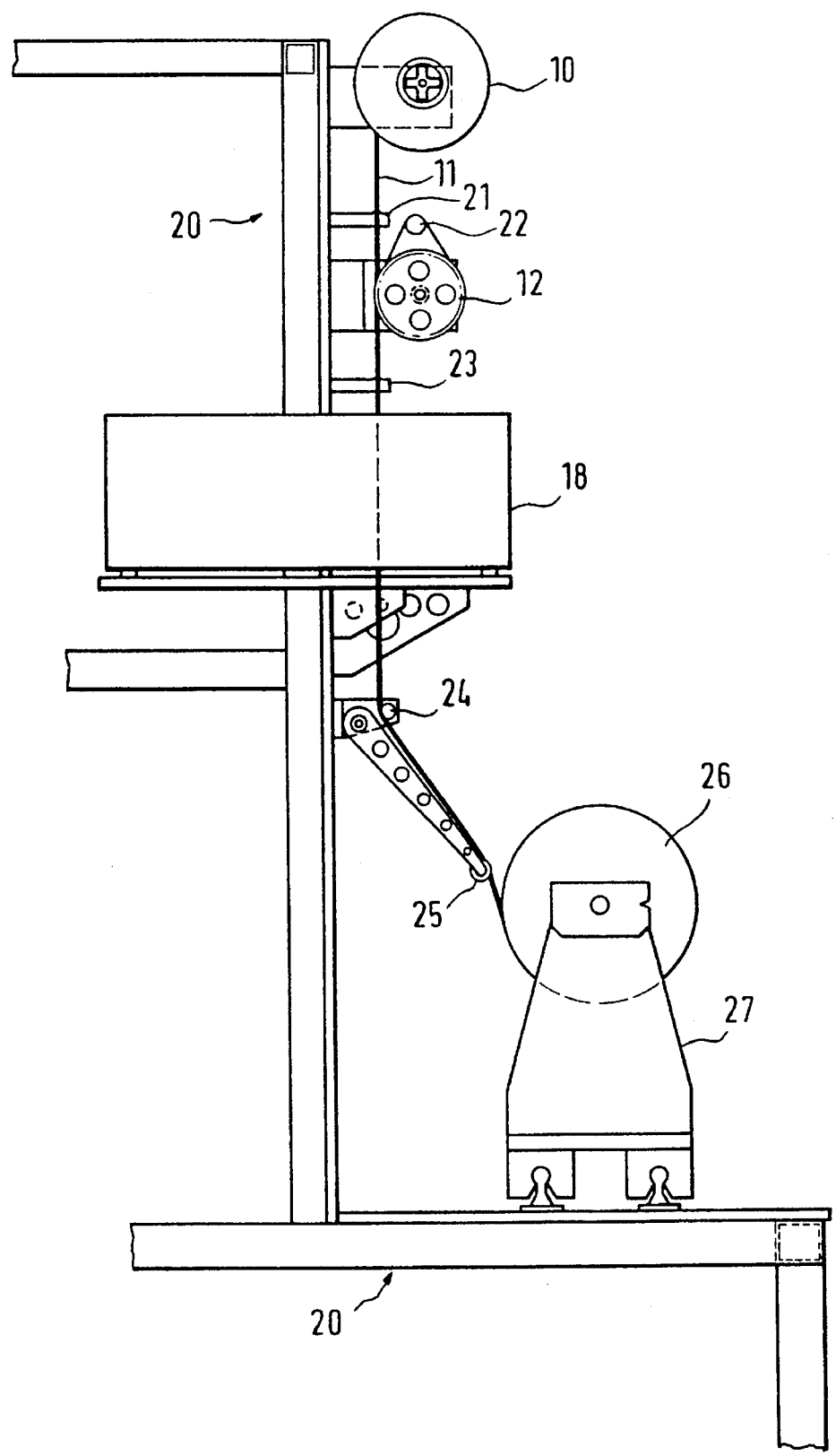
FIG. 5 is a side elevational view of the suture winding apparatus of the present invention.

FIG. 5 illustrates a side view of the suture handling apparatus. Suture storage spool 10 is rotatably mounted at the top of mounting frame 20. Suture 11 is drawn off and passes through guide 21, around capstan 12 and over and around guide roller 22. Suture 11 then passes through a second guide member 23, through laser micrometer 18 where the x-y measurements are made, around guide rollers 24 and 25, and finally onto drum 26. Drum 26 is mounted onto drum mounting frame 27 and is driven to receive suture 11 and maintain tension thereon. During winding of the suture onto drum 26, drum mounting frame 27 traverses in the plane perpendicular to FIG. 5 so that the suture is continuously wound around the drum in a helix from one end of the drum to the other with no two adjacent suture portions touching.

Figure 6:
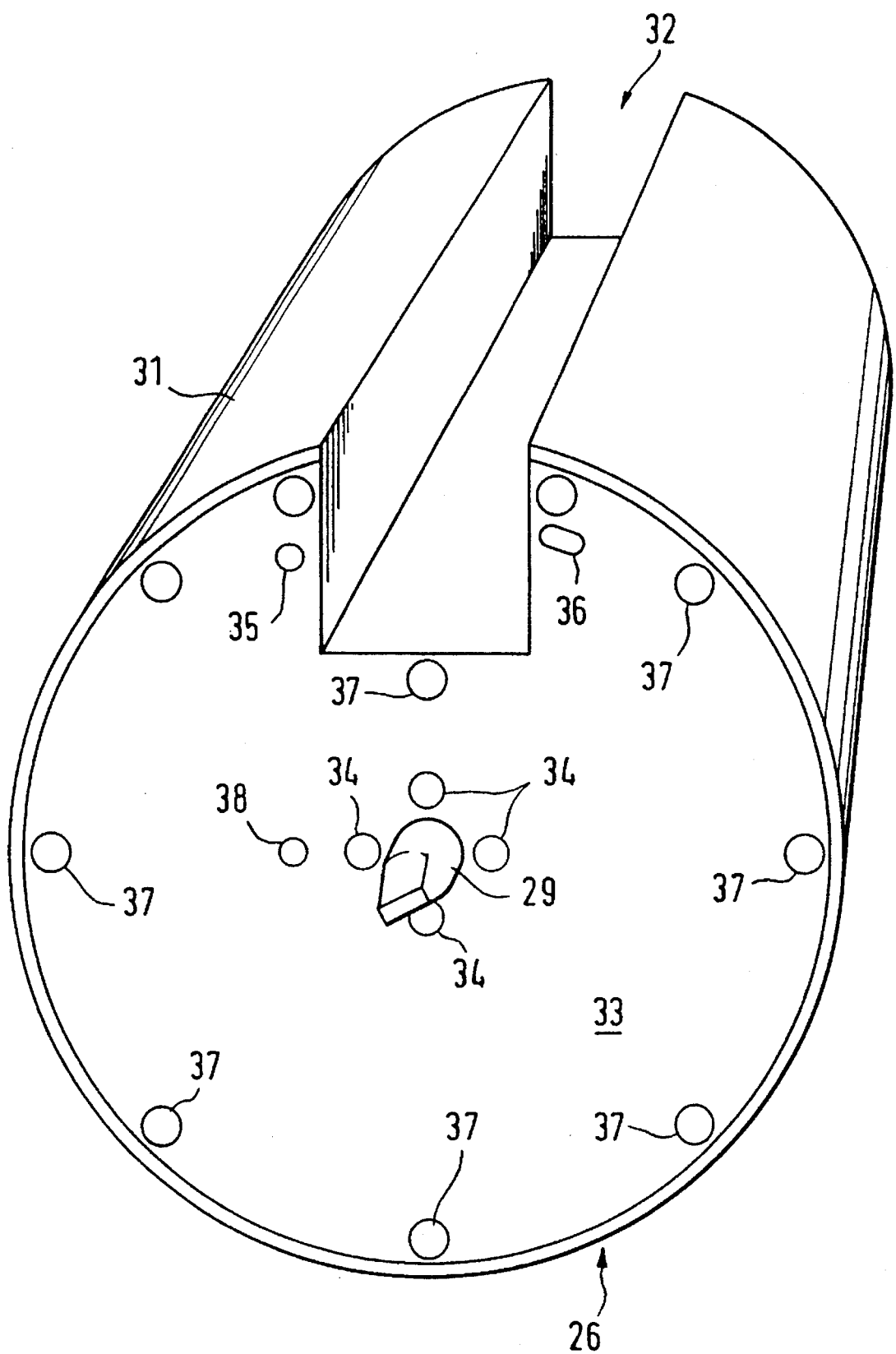
FIG. 6 is a perspective view of the suture winding drum of the present invention.
Figure 6A:
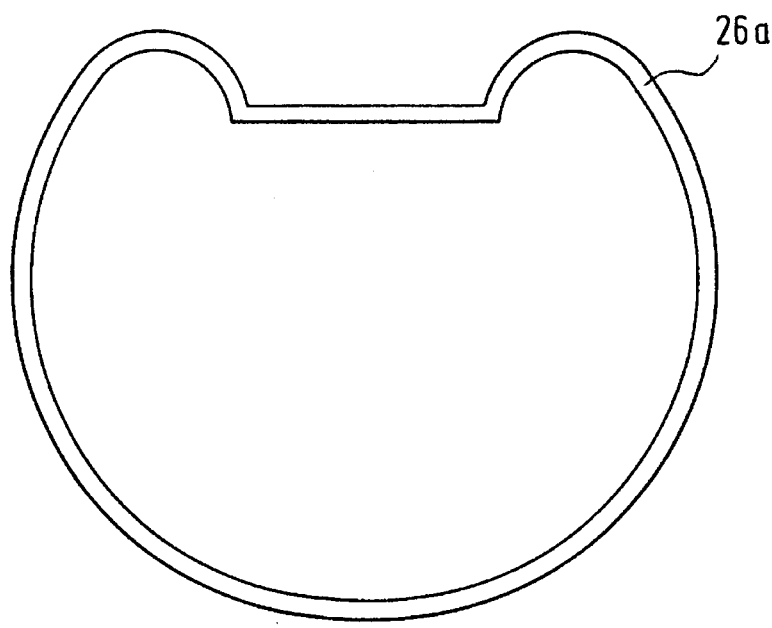
FIG. 6A is an end view of a rib configuration associated with the suture winding drum.

FIGS. 6 and 7 illustrate the drum assembly 26 in greater detail. Referring to FIG. 6, the drum assembly comprises a substantially cylindrical drum 26 having a smooth circumferential surface 31. In order to facilitate gentle treatment of the sutures, the drum may be made of polished stainless steel or stainless steel covered with a silicon rubber skin. Most preferably, drum 26 is fabricated from high density polyethylene with steel end plates. High density polyethylene has been found to be particularly advantageous since excess cyanoacrylate does not adhere to this material during the tipping operation. Where the drum is constructed of high density polyethylene it further has been found desirable to reinforce the drum against deformation by providing a plurality of gussets or ribs inside the drum. An end view of one appropriate rib configuration is shown in FIG. 6A. Each rib has a thickness of about ¼ to ¾ inches in the direction perpendicular to the plane of FIG. 6A. The number of ribs may vary, but two to five ribs should be appropriate, and three ribs are preferred. Drum 26 could also be fabricated from a solid block of high density polyethylene, but the added weight of such a construction most likely will not be desired.

Figure 6B:
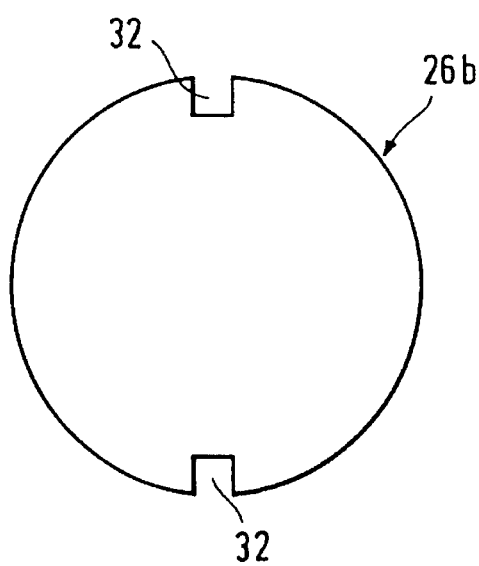
FIGS. 6B and 6C show end elevational views of drums having 2 and 3 notches, respectively.
Figure 6C:
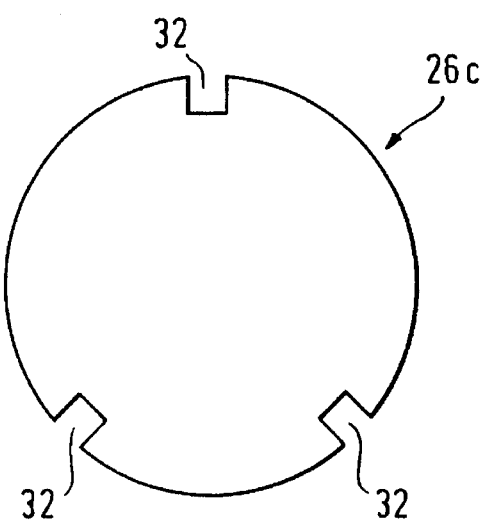

Referring again to FIG. 6, a notch 32 extends lengthwise along the drum. When suture 11 is wound around the drum a portion of each suture wrap will extend across the notch orthogonally to the lengthwise orientation of the notch. The end plate 33h has central apertures 34 and an axial spindle 29 by which the drum can be mounted to fixture 27 such that the drum can be rotated to wind suture 11 thereon. Apertures 35 and 36 are ,for mounting the suture retainer clamps to hold the tipped sutures in place while the tipped section is cut to remove the sutures from the drum, as described below. Peripheral apertures 37 are for attachment of the end plates to the drum, such as by screw mounting, and aperture 38 is provided to receive a positioning pin on the tipping apparatus to hold the drum in the correct orientation during tipping. Of course, drums of different circumference can be made in order to provide tipped sutures of different lengths. By way of example only, drums having a circumference of thirty six, thirty, twenty four and eighteen inches are contemplated. The cylindrical construction of the drum has the added advantage of being conducive to providing multiple longitudinal notches on drums of different circumference in order to be able to tip a variety of different length sutures in a single tipping operation. FIGS. 6B and 6C show end elevational views of drums 26B and 26C having 2 and 3 notches, 32, respectively. It is contemplated that drums having the following general dimensions (inches) could be provided.

| Drum Circumference | Number of Notches | Tipped Suture Lengths |
| --- | --- | --- |
| 15 | 3 | 5 |
| 16 | 2 | 8 |
| 24 | 2 | 12 |

SPRAY TIPPING APPARATUS

The present invention contemplates tipping a suture by passing the portion of the suture to be tipped through a mist or cloud of rapidly curing material, such as the cyanoacrylate monomer described above. The cyanoacrylate monomer is absorbed into the suture braid matrix and usually cures almost immediately. Misting of the cyanoacrylate monomer is achieved by passing it through an atomization nozzle which atomizes the liquid monomer by means of sonic/ultrasonic vibration. The tipping process is described more fully as follows.

Figure 14:
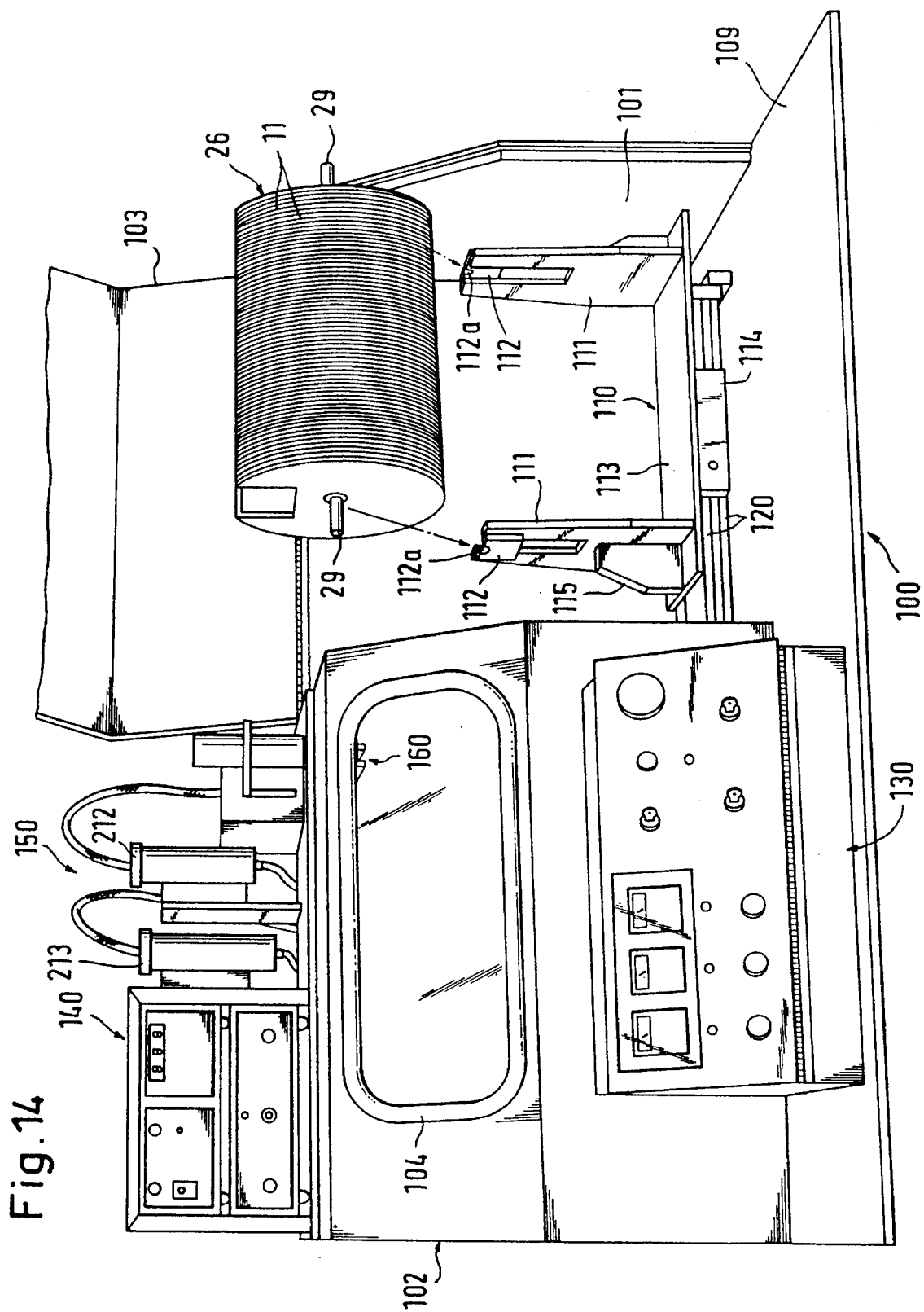
FIG. 14 is a perspective view of the suture tipping apparatus of the present invention.
Figure 15:
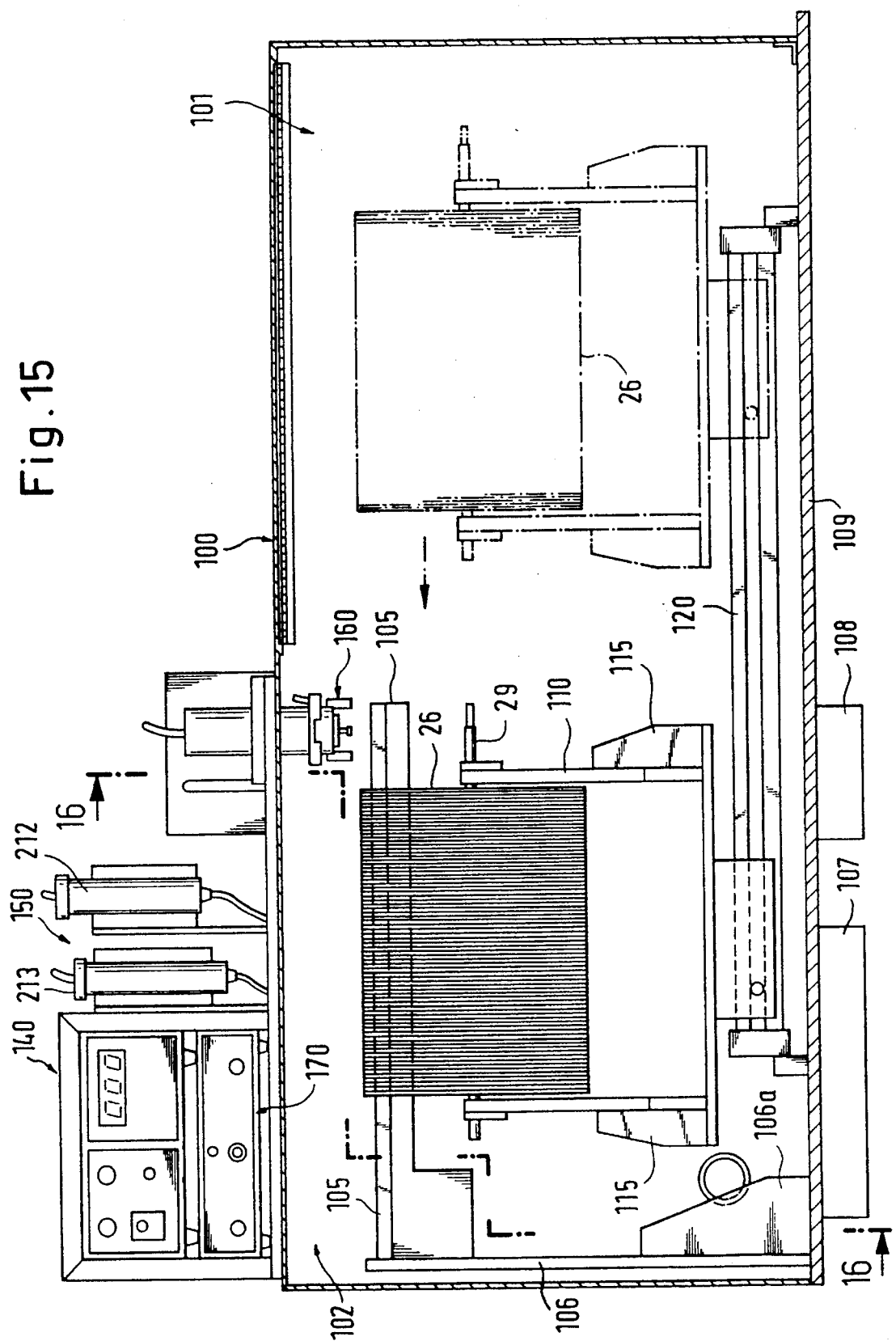
FIG. 15 is a cut away front elevational view of the suture tipping apparatus of the present invention.
Figure 16:
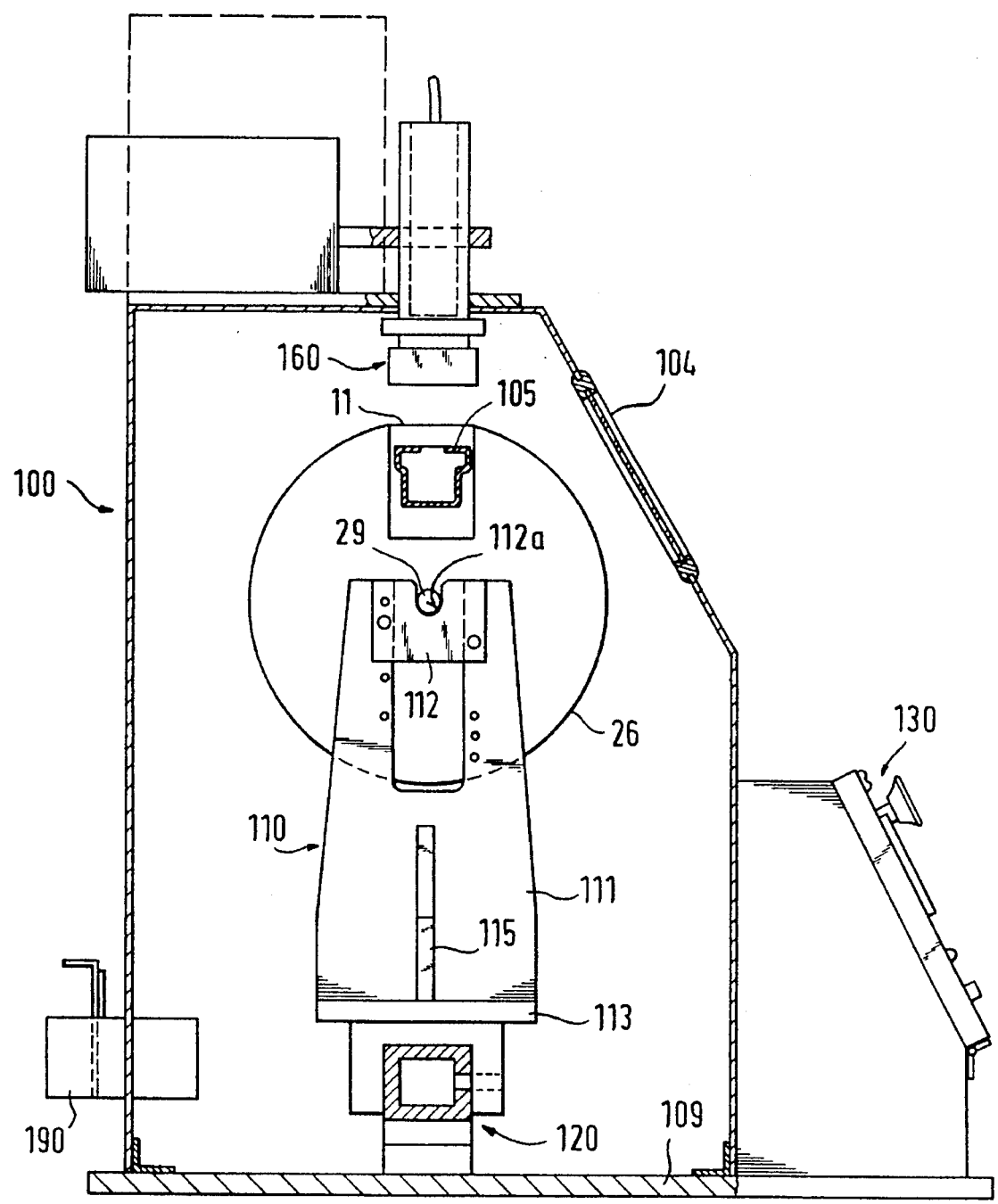
FIG. 16 is a cut away side elevational view of the suture tipping apparatus of the present invention.

After the suture 11 has been wound on drum 26, the drum may be transferred to an apparatus 100 for tipping the suture. Such an apparatus is illustrated in FIGS. 14, 15, and 16, which are now referred to. Drum assembly 26 with suture 11 wound thereon is mounted onto drum mounting carriage 110 in the loading chamber 101 of the suture tipping apparatus 100. Drum mounting carriage 110 has twin uprights 111, each upright having a drum support plate 112 with notches 112a for receiving spindles 29 of the drum. Mounting carriage 110 also has a base 113 with a lower member 114 for slidably engaging rail 120 which extends longitudinally from the loading chamber 101 to the processing chamber 102. The loading chamber 101 may be accessed by means of cover panel 103 which can be pivoted upward to open the loading chamber 101. The tipping apparatus further includes a control panel 130, window 104, sonic control unit 140, liquid storage and transmission system 150, metering control system 170, exhaust port 190 (FIG. 16) for removing vapors of tipping agent and solvents, and a spray head assembly 160. The liquid storage system 150 includes solvent reservoir 213 and tipping solution reservoir 212 and associated transmission lines as discussed below with reference to FIG. 20. A plenum member 105 connected to a source of vacuum extends longitudinally within processing chamber 102 to a point below the spray head assembly 160. Plenum 105 is supported by plenum mount 106, which is braced by gusset 106a. Long and short manifolds 107 and 108, respectively, are below base 109. At the top of the unit 100 the sonic control unit 140 is a sonic/ultrasonic frequency signal generator. The signal is sent to the atomizer nozzle 161 of spray head assembly 160 described below. Atomizer nozzle 161 is the outlet for the tipping solution which creates a fine mist for spraying the suture. The electric signal from sonic control unit is transmitted by conductive wire to piezoelectric elements in the atomizer nozzle. A fluid passing through the nozzle is thereby atomized into a fine mist.

A device suitable for use as the sonic control unit 140 in the present invention is manufactured by Sono-Tek Corporation of 313 Main Mall, Poughkeepsie, N. Y..

The advantage to using sonic/ultrasonic atomization as opposed to pressurized spray is that lower flow velocities may be used. This eliminates bounceback of the sprayed material from the workpiece, which is a problem With pressure spraying. Another advantage of sonic/ultrasonic atomization over pressure atomization is that the outlet orifice diameter of the sonic/ultrasonic atomizer nozzle can be relatively wide while still providing a suitable mist of tipping agent. This helps prevent clogging of the orifice.

Figure 17:
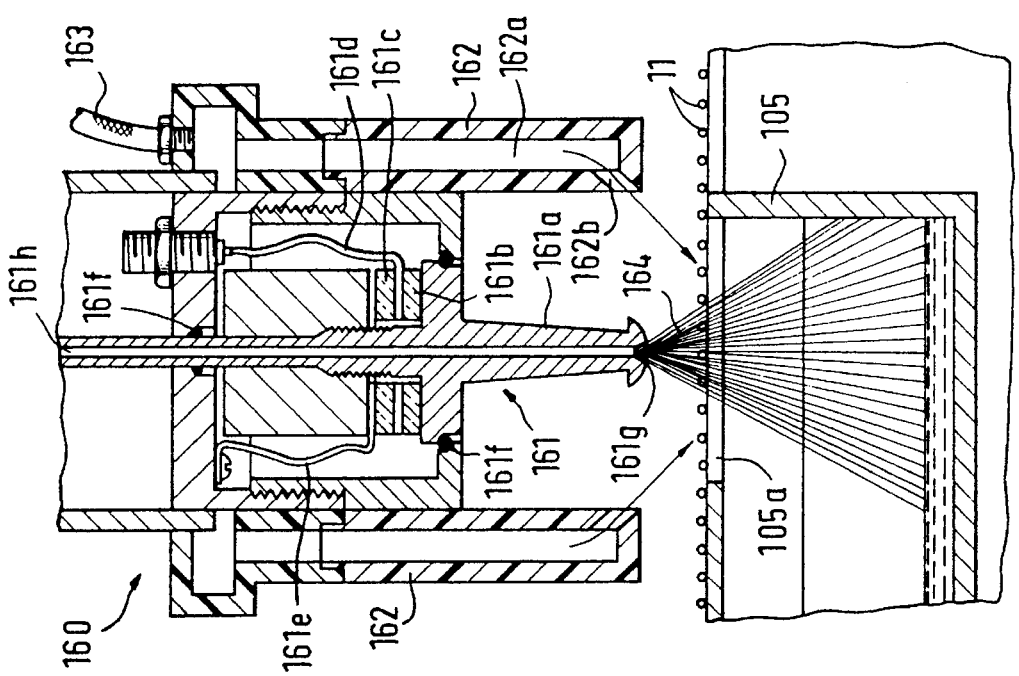
FIG. 17 is a front sectional view of the spray head assembly of the suture tipping apparatus.
Figure 19:
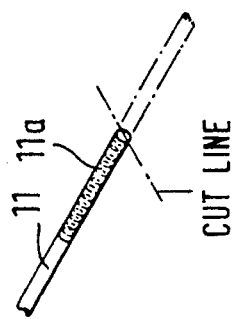
FIG. 19 is a perspective view of a suture with a tipped portion.
Figure 18:
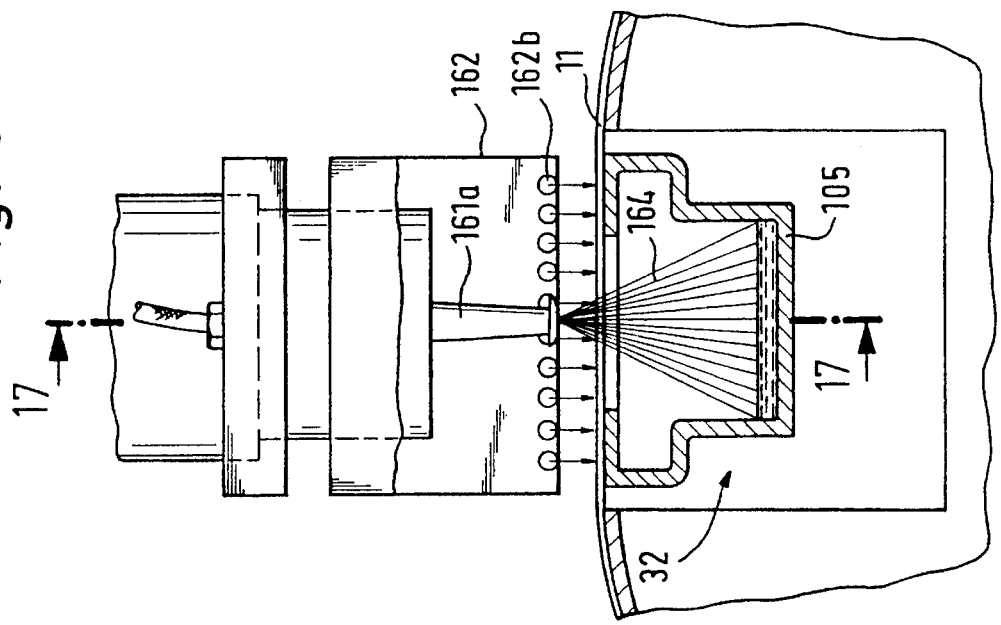
FIG. 18 is a partially cut away side view of the spray head assembly of the suture tipping apparatus.

Yet another advantage is that the atomization creates a cloud or mist which, when the suture is passed through, coats and saturates all sides of the suture, not just the side of the suture facing the outlet orifice of the atomizer. Thus, the application of tipping agent is not limited by line of sight impingement of tipping agent onto the suture, as would be the case with simple spray application. Referring now to FIGS. 17 and 18, the spray head assembly 160 includes spray nozzle 161, which comprises a downwardly projecting member 161a having an internal bore 161h terminating in orifice outlet 161g. The cyanoacrylate tipping agent passes through said bore and is atomized to a fine mist 164 upon exiting the nozzle. Atomization is achieved by means of piezoelectric elements 161b and 161c which are electrically connected via wires 161d and 161e respectively to the Sono-Tek signal generating unit 140. The signals from the unit 140 may be varied in frequency to adjust the fineness of the mist. O-rings 161f provide a seal for the atomization nozzle 161.

Blocks 162 have an internal chamber for an inert gas such as nitrogen, which is fed in through gas line 163. The gas exits via apertures 162b in the bottom of the blocks 62.

Plenum member 105 has an aperture 105a positioned below the atomizer nozzle 161 so as to catch any excess spray. The aperture also permits the suture to be surrounded by the mist so that the entire suture, including the underside of the suture, is uniformly coated with the cyanoacrylate monomer.

Figure 20:
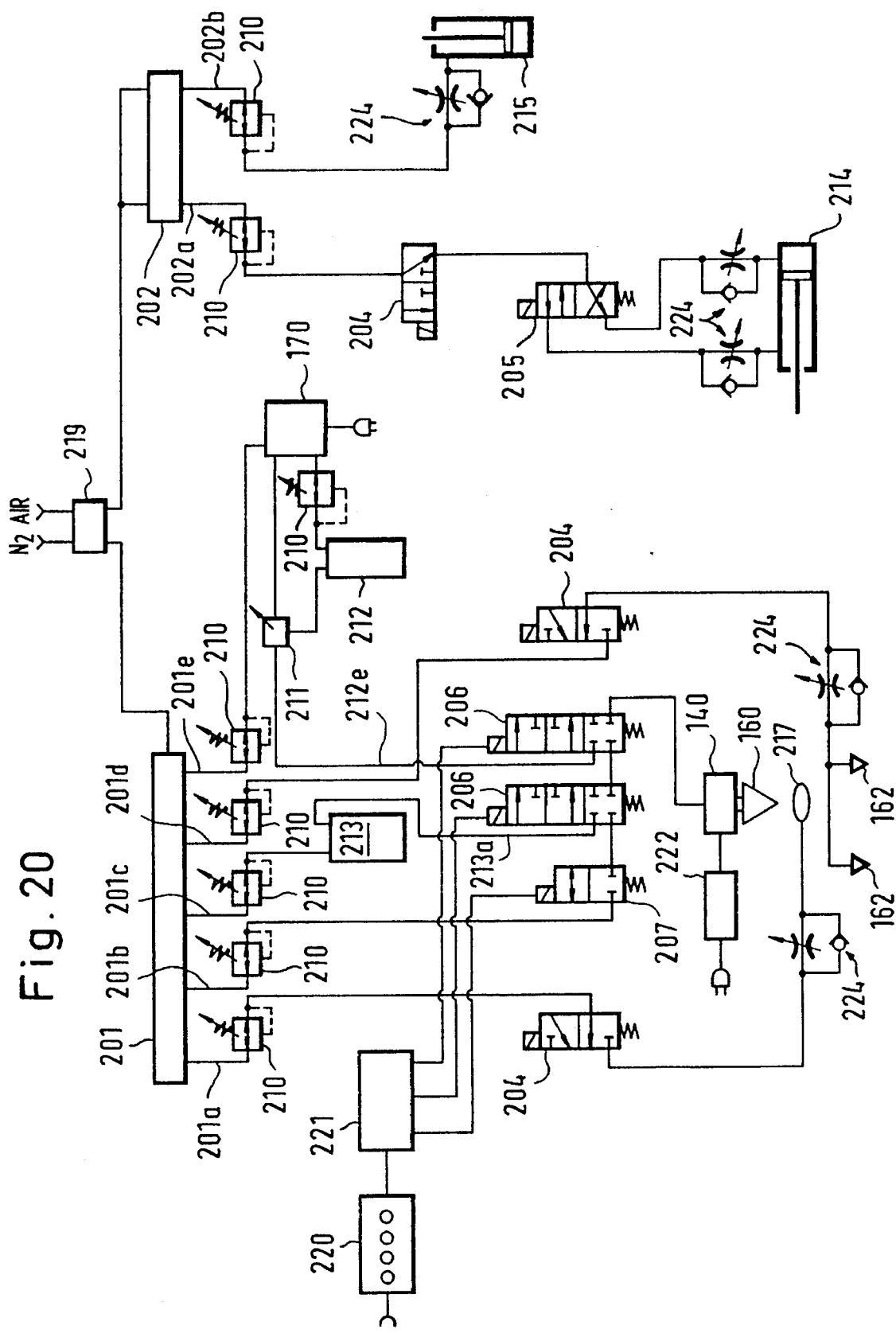
FIG. 20 is a schematic illustration of the suture tipping system of the present invention.

FIG. 20 is a schematic flow chart of the tipping system. Gas supply 219 is a source of inert gas, preferably nitrogen. Optionally, a source of compressed air may be provided with air being fed to the ports between tipping cycles, i.e. when the instrument is not being used. Nitrogen is sent to five port manifold 201 where it is distributed by regulators 210 at each port to the various parts of the system. Line 201*a* is distributed through 3-way valve 204 to spray ring 217. Optional switch 224 activates the optional supply of air to the ports when the tipping apparatus is inactive. Line 201*b* is distributed through 2-way valve 207 and two 3-port flow through 206 to the ultrasonic atomization nozzle 160 for blowing through the orifice 161*g* in a clearing procedure. Line 201*c* is distributed to the solvent reservoir 213 for pressurization.

Line 213*a* from the solvent reservoir carries solvent such as acetone, methylethylketone, or preferably 1,1,1-trichloroethane. The solvent is used to flush residual cyanoacrylate tipping agent from the system. Line 201*d* carries nitrogen through 3-way valve 204 to the inert gas chamber 162. Line 201*e* carries nitrogen through metering system 170 and regulator 210 to pressurize the tipping agent storage bottle 212. The tipping agent is carried via line 212*e* through 3-port flow through 206 to the atomizing nozzle 160 where it is misted and sprayed onto a suture.

Pressurized air is sent to 2-port manifold 202 and carried via line 202*a* through regulator 210 and 3-way valve 204 and 4-way valve 205 to power the carriage drive 214 from moving the drum mounting carriage 10. Compressed air is also sent via line 202*b* through a regulator 210 to a mechanism 215 for opening and closing cover panel 103.

The tipping procedure is as follows. A drum assembly 26 with suture 11 wound thereon is placed onto the drum mounting carriage in the loading chamber 101 of the apparatus (See FIG. 14). The cover panel 103 is closed and the tipping sequence is initiated on the control panel 130. Compressed air powers the carriage drive 214 to move the carriage 110 and drum assembly into the processing chamber 102. As drum 26 enters chamber 102, plenum member 105 becomes disposed in notch 32 beneath the suture. As the drum assembly 26 moves under the spray head assembly 160, pressurized nitrogen at 2 psi enters the tipping solution supply to bottle 212 and moves the tipping agent to the nozzle 161 where it is atomized by sonic or ultrasonic frequency generated by the Sono-Tek unit 140. Generally a frequency of about 60 cycles is preferred although other frequencies may be selected. The tipping agent is atomized to create a cloud or mist 164 (See FIGS. 17 and 18) which envelopes the sutures as they pass underneath during the traverse of drum 26 into chamber 26. Only those portions of the suture traversing the notch 32 are coated with tipping agent. As the sutures sequentially pass through the mist of tipping agent they are saturated with the agent which begins to cure in a very short period of time, typically in less than a second. The cyanoacrylate cures by polymerization catalyzed by ambient moisture. While the tipping agent is being sprayed nitrogen is blown through apertures 162*b* of inert gas chambers 162 to create a "curtain" of nitrogen gas which blows excess tipping agent from the suture 11 into plenum 105 to be drawn off under vacuum.

On the return pass of drum 26 from chamber 102 to chamber 101 the suture again passes underneath the nozzle and, optionally, an additional tipping application can be made during this pass. Alternatively, several passes back and forth underneath the nozzle can be made to apply tipping agent several times. When the procedure is completed, the drum support carriage returns to the loading chamber 101, and solvent from reservoir 213 is flushed through the system to clear out residual tipping agent. Thereafter, nitrogen is flushed through the atomizing head to clear out any residual solvent.

The tipping agent is preferably a solution of ethylcyanoacrylate monomer in methylethylketone (MEK). Approximately 250 milliliters of MEK is added to 8 ounces of ethylcyanoacrylate to adjust the viscosity of the tipping agent to a range of from about 2 to 3 centipoise. Methylene chloride is also an acceptable solvent.

Alternatively various other materials can be added to the tipping solution. For example, an bioabsorbable copolymer of glycolide and lactide may be dissolved in the tipping solution to form a biodegradable coating on the suture braids. If such an additive is employed the amount of MEK may have to be adjusted to keep the viscosity of the tipping solution within a range of about 2 to 3 centipoise. Too high a viscosity makes atomization of the tipping agent more difficult, and inhibits wicking or absorption of the tipping agent into the filaments of the braided suture. Referring to FIG. 19, the tipped portion 11*a* of suture 11 is usually fully polymerized and dried in about 20 to 30 seconds.

CUTTING THE TIPPED SUTURES FROM THE DRUM

After the tipping solution has polymerized, the tipped suture may be removed from the drum by cutting the tipped suture, such as with a scissors or by passing a razor or knife blade across the tipped portion to create suture segments having two tipped ends suitable for use in conjunction with a surgical needle as explained above with reference to FIGS. 1 to 3.

In order to facilitate controlled cutting and removal of the tipped sutures from the drum, removable drum clamps are provided to be mounted onto the drum after tipping is complete.

A drum clamp 40 is illustrated in side view in FIG. 7. As explained below, suture clamp 40 is mounted to drum 26 after the suture 11 has been tipped in order to retain the suture in place during removal of the suture from the drum. Suture clamp 40 includes a main support 41 which is a U-shaped elongated member having mounting apertures 41*a*, as illustrated in FIG. 8. Referring again to FIG. 7, suture clamp 40 also includes dowel arm support 42 as illustrated in perspective view in FIG. 9. Dowel arm support 42 has dowel apertures 42*a* for receiving dowels 48 which provide means for mounting the dowel support arm to the main support 41. At least one aperture 42*b* on the dowel arm support accepts button screw 49*a*for mounting dowel arm 43 to dowel arm support 42*a*.

Referring additionally to FIG. 10, dowel arm 43 includes an elongated aperture 43*a* through which button screw 49*a*extends for mounting to aperture 42*b* on the dowel arm support. Aperture 43*b* retains dowel 47 for mounting into aperture 35 of drum 26, as will be explained below.

Suture clamp 40 further includes a rocker clamp support 44 shown in FIGS. 7 and 11, which includes a knurled portion 44*a* , an aperture 44*b*for accepting a button screw 49*b*for mounting a rocker clamp 45, an aperture 44*c*for receiving a dowel 48 for mounting to main support 41, and another aperture (not shown in FIG. 11) for receiving a button screw 49*c*for mounting rocker spring 46 to the rocker clamp support (See FIG. 7).

Referring now to FIG. 12, rocker clamp 45 includes an elongated aperture 45*a*for receiving button screw 49*b*for mounting the rocker clamp to rocker clamp support 44. The downwardly extending leg portion of rocker clamp 45 includes a hook 45*b* for mounting into an elongated aperture 36 in the drum, in a manner to be described below.

Referring to FIGS. 7 and 13, a rocker spring 46 mounts to the underside of rocker clamp support 44 by means of button screw 49c which extends through aperture 46a and into a receiving aperture in the rocker clamp support 44.

The undersurface of the suture clamp 44 comprises a layer of soft resilient material 50 for contacting the suture and holding the suture to the surface of the drum 30. The preferred material for layer 50 is a silicone rubber material available from CHR Industries, New Haven, Conn., under the designation COHRlastic 9275. The material is preferably of low modulus (soft). The thickness of the foam can range from about 30 to 500 mils and is preferably about 100 to 150 mils.

Figure 21:
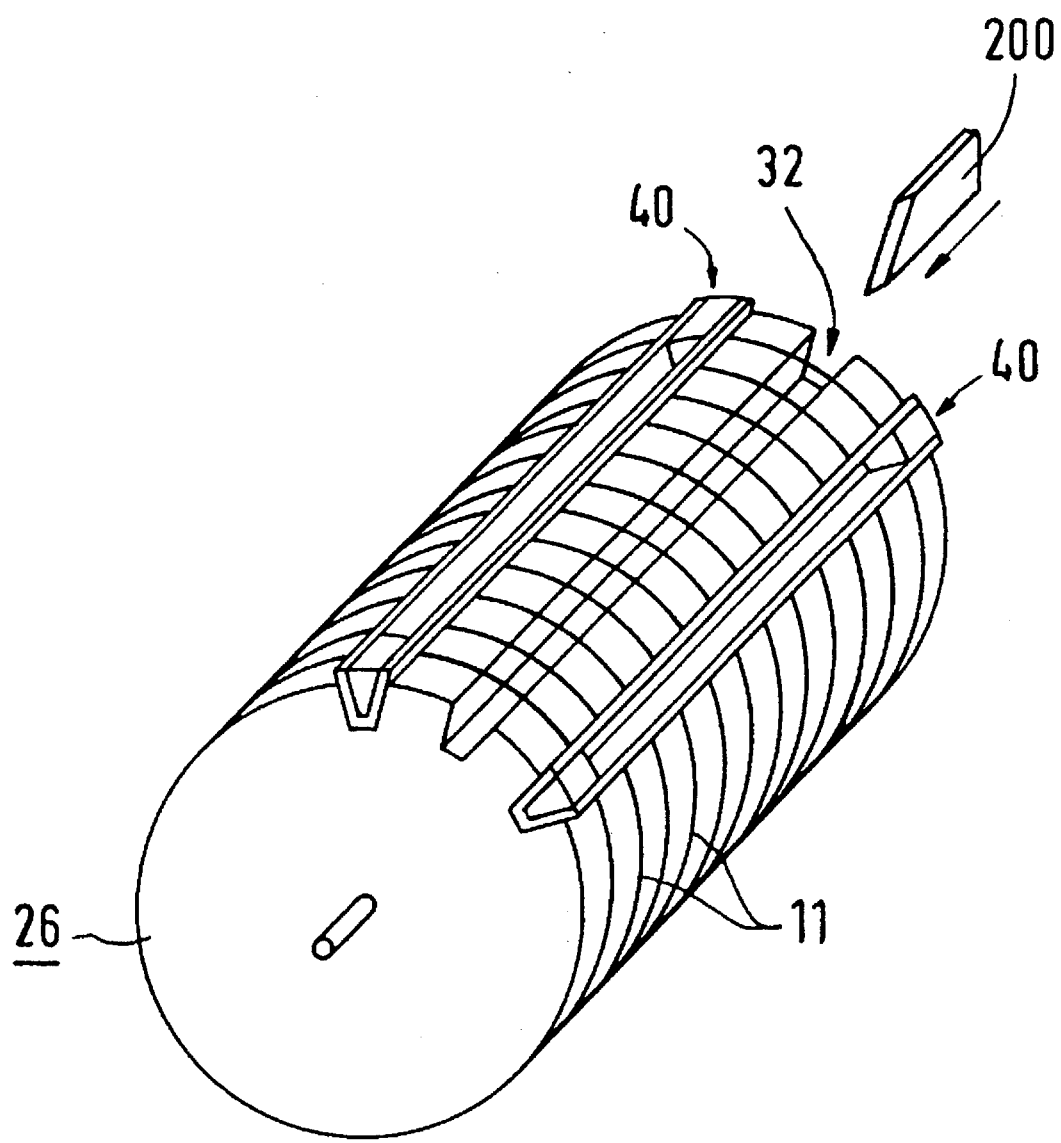
FIG. 21 illustrates the placement of clamps on the drum to secure the suture for a cutting procedure.

In use, after suture material 11 is wound onto drum 26 on winding apparatus 20 and the sutures have been tipped, such as by tipping apparatus 100, a pair of suture retaining clamps 40 are mounted to the drum on either side of notch 32 extending longitudinally parallel thereto, as illustrated in FIG. 21. The clamps are mounted in opposite orientation to one another, and are mounted by engaging dowel 47 into aperture 35 of drum 26 (see FIGS. 6 and 7a), and thereafter engaging rocker clamp hook 45b in elongated slot or aperture 36 on the drum. Hook 46b is biased by spring 46 into engagement with elongated slot 36. With clamps 40 mounted on either side of notch 32, the tipped suture segment can be cut by knife 200 down the longitudinal length of notch 32. Because clamps 40 retain each end of the cut suture against the drum adjacent to the notch, the sutures do not fall uncontrolled away from the drum. After the suture has been cut, knurled portion 44a is pressed to overcome spring 46 and release hook 45b from slot 36, thereby releasing the cut sutures from the drum in a controlled manner.

It is also contemplated that clamps 40 could be mounted onto drum 26 prior to tipping and remain in place during tipping of the sutures and removal of the tipped sutures from the drum.

What is claimed is:

1. In a length of multifilament surgical suture, the improvement comprising at least one end of said multifilament surgical suture tipped with substantially fully cured cyanoacrylate.

2. The suture of claim 1 wherein said surgical suture is a filled suture.

3. The suture of claim 2 wherein said suture is filled with a glycerol containing filler.

4. The suture of claim 1 wherein said suture is coated with at least one lubricant coating.

5. The suture of claim 4 wherein said lubricant coating is a copolymer of glycolide, lactide and polyethylene oxide.

6. In a length of multifilament surgical suture coated with a lubricant coating; the improvement comprising at least one end of said coated multifilament surgical suture tipped with substantially fully cured cyanoacrylate.

7. The suture of claim 6 wherein said surgical suture is a filled suture.

8. The suture of claim 6 wherein said suture is filled with a glycerol containing filler.

9. The suture of claim 6 wherein said lubricant coating is a copolymer of glycolide, lactide and polyethylene oxide.

* * * * *